(12) United States Patent
Petrzilek et al.

(10) Patent No.: US 10,737,101 B2
(45) Date of Patent: Aug. 11, 2020

(54) MEDICAL DEVICE CONTAINING A SOLID ELECTROLYTIC CAPACITOR

(71) Applicant: AVX Corporation, Fountain Inn, SC (US)

(72) Inventors: Jan Petrzilek, Usti nad Orlici (CZ); Martin Trojan, Trebic (CZ)

(73) Assignee: AVX Corporation, Fountain Inn, SC (US)

( * ) Notice: Subject to any disclaimer, the term of this patent is extended or adjusted under 35 U.S.C. 154(b) by 0 days.

(21) Appl. No.: 15/810,456

(22) Filed: Nov. 13, 2017

(65) Prior Publication Data
US 2018/0133493 A1   May 17, 2018

Related U.S. Application Data

(60) Provisional application No. 62/421,425, filed on Nov. 14, 2016.

(51) Int. Cl.
| | |
|---|---|
| *A61N 1/375* | (2006.01) |
| *H01G 9/15* | (2006.01) |
| *H01G 9/052* | (2006.01) |
| *H01G 9/07* | (2006.01) |
| *H01G 9/26* | (2006.01) |
| *H01G 9/012* | (2006.01) |
| *H01G 9/025* | (2006.01) |
| *H01G 9/14* | (2006.01) |
| *H03B 5/12* | (2006.01) |

(Continued)

(52) U.S. Cl.
CPC ......... *A61N 1/37512* (2017.08); *H01G 9/012* (2013.01); *H01G 9/025* (2013.01); *H01G 9/052* (2013.01); *H01G 9/07* (2013.01); *H01G 9/14* (2013.01); *H01G 9/26* (2013.01); *H03B 5/1265* (2013.01); *A61N 1/3981* (2013.01); *A61N 1/39622* (2017.08); *H01G 4/38* (2013.01); *H01G 9/15* (2013.01)

(58) Field of Classification Search
None
See application file for complete search history.

(56) References Cited

U.S. PATENT DOCUMENTS

| | | | |
|---|---|---|---|
| 5,111,327 A | 5/1992 | Blohm et al. | |
| 5,849,025 A | 12/1998 | Owens et al. | |

(Continued)

FOREIGN PATENT DOCUMENTS

JP   2012174948 A   9/2012

OTHER PUBLICATIONS

International Search Report and Written Opinion PCT/US2017/061426 dated Feb. 5, 2018, 11 pages.

(Continued)

*Primary Examiner* — Dion Ferguson
(74) *Attorney, Agent, or Firm* — Dority & Manning, P.A.

(57) ABSTRACT

A capacitor bank for use in a medical device is provided. Through selective control over the individual capacitors employed in the bank, a low ESR can be achieved without adversely impacting other properties of the resulting medical device. More particularly, at least one capacitor in the bank may contain a solid electrolytic capacitor element that includes an anode and a solid electrolyte overlying the anode. The anode includes an anodically oxidized, sintered porous pellet and the solid electrolyte includes a plurality of conductive polymer particles.

16 Claims, 4 Drawing Sheets

(51) Int. Cl.
*A61N 1/39* (2006.01)
*H01G 4/38* (2006.01)

(56) References Cited

U.S. PATENT DOCUMENTS

| | | | |
|---|---|---|---|
| 6,197,252 B1 | 3/2001 | Bishop et al. | |
| 6,635,729 B1 | 10/2003 | Groenendaal et al. | |
| 6,674,635 B1 | 1/2004 | Fife et al. | |
| 6,786,951 B2 | 9/2004 | He et al. | |
| 6,795,729 B1* | 9/2004 | Breyen | A61N 1/375 607/5 |
| 6,987,663 B2 | 1/2006 | Merker et al. | |
| 7,099,143 B1 | 8/2006 | Fife et al. | |
| 7,150,776 B2 | 12/2006 | Shekhter et al. | |
| 7,169,284 B1 | 1/2007 | Jiang et al. | |
| 7,256,982 B2* | 8/2007 | Lessner | H01G 9/042 361/503 |
| 7,262,511 B2 | 8/2007 | Osako et al. | |
| 7,667,954 B2 | 2/2010 | Lessner et al. | |
| 7,684,171 B2 | 3/2010 | Rorvick et al. | |
| 7,952,853 B2 | 5/2011 | Viste et al. | |
| 8,023,250 B2 | 9/2011 | Ning et al. | |
| 8,313,538 B2 | 11/2012 | Merker et al. | |
| 8,477,479 B2 | 7/2013 | Pease et al. | |
| 8,675,348 B2 | 3/2014 | Viste et al. | |
| 8,687,347 B2 | 4/2014 | Bates et al. | |
| 8,824,121 B2 | 9/2014 | Biler et al. | |
| 9,053,854 B2 | 6/2015 | Petrzilek et al. | |
| 9,105,401 B2 | 8/2015 | Dreissig et al. | |
| 9,324,503 B2 | 4/2016 | Biler et al. | |
| 9,620,293 B2 | 4/2017 | Djebara et al. | |
| 9,620,294 B2 | 4/2017 | Djebara et al. | |
| 9,786,440 B2 | 10/2017 | Weaver et al. | |
| 9,824,826 B2 | 11/2017 | Petrzilek et al. | |
| 10,026,521 B2 | 7/2018 | Scheel et al. | |
| 2004/0064155 A1* | 4/2004 | Norton | H01G 9/155 607/5 |
| 2005/0162810 A1* | 7/2005 | Seitz | A61N 1/375 361/328 |
| 2005/0264979 A1* | 12/2005 | Breyen | A61N 1/375 361/517 |
| 2006/0061938 A1* | 3/2006 | Dombro | H01G 2/106 361/502 |
| 2010/0134955 A1* | 6/2010 | O'Connor | A61N 1/375 361/508 |
| 2012/0039019 A1 | 2/2012 | Zednickova | |
| 2012/0106031 A1* | 5/2012 | Vilc | H01G 2/10 361/525 |
| 2012/0134073 A1* | 5/2012 | Uher | H01G 9/028 361/528 |
| 2014/0067303 A1* | 3/2014 | Millman | G01R 31/016 702/84 |
| 2015/0049419 A1 | 2/2015 | Biler et al. | |
| 2016/0148757 A1 | 5/2016 | Djebara et al. | |
| 2016/0189876 A1 | 6/2016 | Djebara et al. | |
| 2017/0280563 A1* | 9/2017 | Vaillancourt | H01G 9/07 |
| 2018/0137985 A1 | 5/2018 | Petrzilek et al. | |
| 2018/0137989 A1 | 5/2018 | Petrzilek et al. | |

OTHER PUBLICATIONS

European Search Report for 17868885.9 dated Jun. 6, 2020, 8 pages.

* cited by examiner

MEDICAL DEVICE CONTAINING A SOLID ELECTROLYTIC CAPACITOR

CROSS REFERENCE TO RELATED APPLICATION

The present application claims filing benefit of U.S. Provisional Patent Application Ser. No. 62/421,425 having a filing date of Nov. 14, 2016, and which is incorporated herein by reference in its entirety.

BACKGROUND OF THE INVENTION

High voltage capacitors are often employed in implantable medical devices. Implantable cardioverter defibrillators ("ICDs"), for instance, normally employ a capacitor bank that contains two to four capacitors connected in series to achieve a high therapeutic voltage for shock delivery. In certain cases, for instance, the capacitor may contain a metal foil (e.g., aluminum foil) in combination with a liquid electrolyte having a relatively neutral pH. One problem, however, is that these types of electrolytes tend to increase the equivalent series resistance ("ESR") of the capacitor, which can result in wasted energy when the bank delivers a therapeutic high voltage treatment. As such, a need currently exists for improved capacitors for use in a medical device, such as a defibrillator.

SUMMARY OF THE INVENTION

In accordance with one embodiment of the present invention, a capacitor bank for a medical device is disclosed. The bank comprises two or more individual capacitors that are connected in series, wherein at least one of the capacitors in the bank comprises a capacitor element that contains an anode and a solid electrolyte. The anode contains a sintered porous pellet and a dielectric layer formed thereon. The solid electrolyte overlies the dielectric layer and contains a plurality of conductive polymer particles. The capacitor also contains an anode termination that is in electrical connection with the anode, a cathode termination that is in electrical connection with the solid electrolyte, and a casing that encapsulates the capacitor element and leaves exposed at least a portion of the anode termination and the cathode termination. In accordance with another embodiment of the present invention, a medical device is disclosed that comprises a capacitor bank provided within a housing. The bank comprises two or more individual capacitors that are connected in series, such as described above.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

Figure 1:
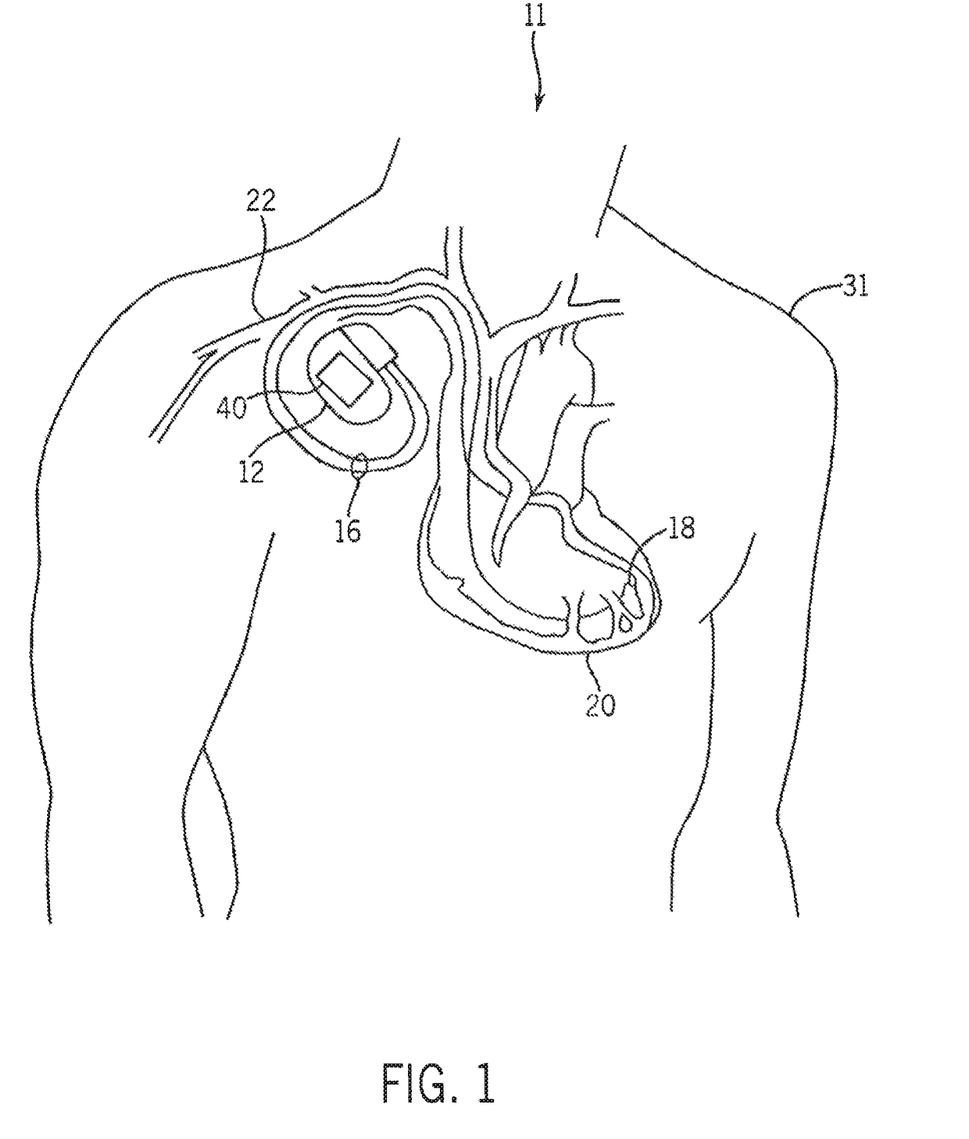
FIG. 1 is a schematic illustration one embodiment of an implantable medical device that may be employed in the present invention, shown in the form of a defibrillator implanted within a human body.
Figure 2:
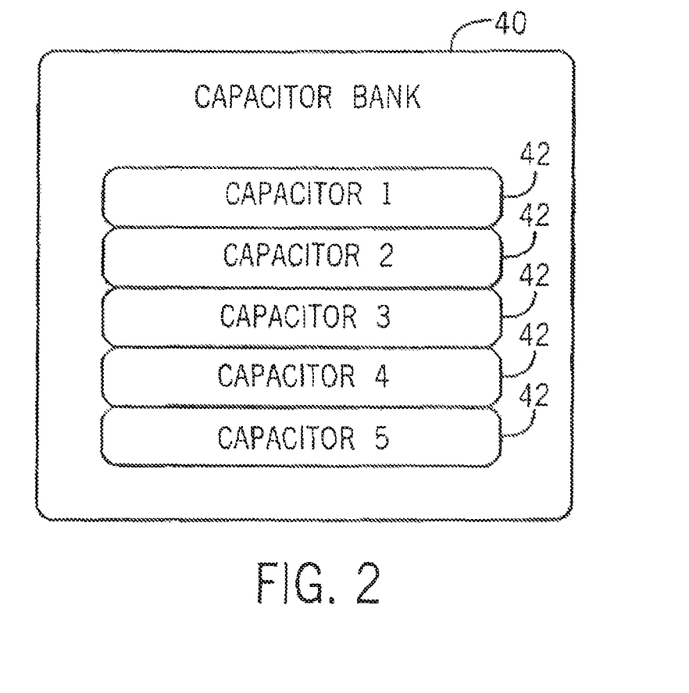
FIG. 2 is a schematic illustration of one embodiment of a capacitor bank that may be employed in an implantable medical device in accordance with the present invention.

Generally speaking, the present invention is directed to a capacitor bank for use in a medical device, such as an implantable defibrillator, pacemaker, cardioverter, neural stimulator, drug administering device, etc. In one embodiment, for example, the capacitor bank may be employed in a medical device that is configured to provide a therapeutic high voltage, such as from about 500 to about 950 volts, and in some embodiments, from about 600 volts to about 900 volts. Referring to FIGS. 1-2, for example, a system 11 is shown that includes a medical device 12 implanted within a body or torso of a patient 31. In this particular embodiment, the device 12 is in the form of a defibrillator. One or more leads 16 are electrically coupled between the device 12 and the patient's heart 20 via a vein 22. Electrodes 18 are provided to sense cardiac activity and/or provide a voltage to the heart 20. At least a portion of the leads 16 (e.g., an end portion of the leads) may be provided adjacent or in contact with one or more of a ventricle and an atrium of the heart 20.

Figure 3:
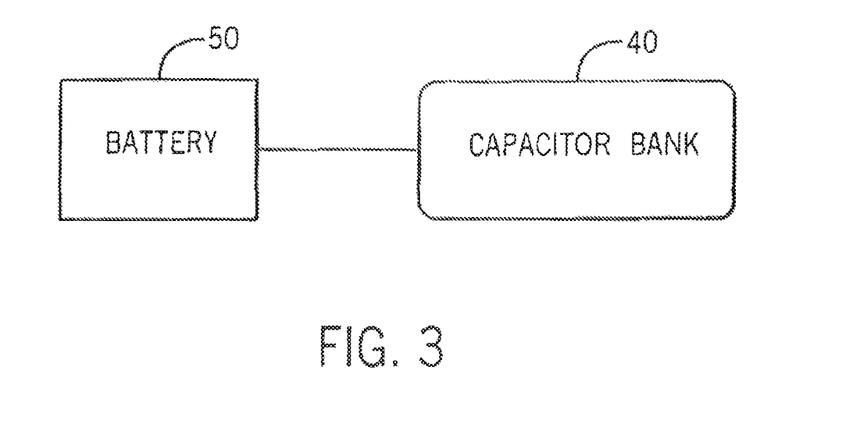
FIG. 3 is a schematic illustration of the capacitor bank of FIG. 2 connected to a battery.

As shown, a capacitor bank 40 is also provided within the device 12. The capacitor bank typically contains at least two (2) capacitors, in some embodiments at least three (3) capacitors, and in some embodiments, from four (4) to fifteen (15) capacitors, which are generally connected in series. In FIG. 2, for example, the capacitor bank 40 contains five (5) individual capacitors 42 connected in series. The capacitor bank may also be provided within a housing (e.g., metal container) that is hermetically sealed and biologically inert. As shown in FIG. 3, the capacitor bank 40 is also typically coupled to a battery 50 that is located within or external to the device 12. The capacitors 42 are generally configured to store energy provided by the battery 50. For example, the system 11 may be configured such that when the device 12 determines that a therapeutic high-voltage treatment is required to establish a normal sinus rhythm for the heart 20, the capacitors 42 are charged to a predetermined charge level by the battery 50. Charge stored in the capacitors 42 may then be discharged via the leads 16 to the heart 20. In other embodiments, the capacitors 42 may be charged prior to determination that a stimulating charge is required by the heart such that the capacitors 42 may be discharged as needed.

The device 12 may be configured to deliver an electric pulse energy (e.g., 30 joules) to the heart 20 for a single defibrillation pulse. However, it should be understood that the therapeutic high voltage treatment delivered to the patient's heart 20 may vary somewhat in intensity depending on the patients' physiology and the details of the particular configuration of device 12. Also, the capacitors 42 may be configured to store energy from battery 50 and discharge that energy in a timely manner. For example, the capacitors 42 may be configured so that the capacitor charge times may be about 10 seconds when using electrical currents of about 10 mA. Also, the capacitors 42 may be configured so that the typical discharge times are about 10 milliseconds. Thus, in one embodiment, the capacitors 42 are configured to deliver about 30 joules of electrical energy in a total time window of about 10 seconds, using a charge current on the order of 10 mA.

To provide the desired charge and discharge times, the individual capacitors and the resulting capacitor bank generally have a low internal resistance or impedance, which is typically characterized by the equivalent series resistance ("ESR") value. For example, the capacitor bank and/or individual capacitors within the bank typically exhibit an ESR of about 5 ohms or less, in some embodiments about 3 ohms or less, and in some embodiments, from about 0.001 to about 1 ohm, measured at an operating frequency of 100 Hz. In this manner, the capacitor bank can provide a timely delivery of the therapeutic high voltage treatment with minimal waste of energy lost in heating the device. The present inventors have discovered that through selective control over the capacitor(s) employed in the bank, such a low ESR can be achieved without adversely impacting other properties of the resulting medical device. More particularly, at least one capacitor (e.g., all of the capacitors) in the bank may contain a solid electrolytic capacitor element that includes an anode and a solid electrolyte overlying the anode. The anode includes an anodically oxidized, sintered porous pellet and the solid electrolyte includes a plurality of conductive polymer particles.

Various embodiments of the present invention will now be described in more detail.

I. Capacitor Element

A. Anode

The pellet may be formed from a valve metal powder that contains a valve metal (i.e., metal that is capable of oxidation) or valve metal-based compound, such as tantalum, niobium, aluminum, hafnium, titanium, alloys thereof, oxides thereof, nitrides thereof, and so forth. For example, the valve metal powder may contain an electrically conductive oxide of niobium, such as niobium oxide having an atomic ratio of niobium to oxygen of 1:1.0±1.0, in some embodiments 1:1.0±0.3, in some embodiments 1:1.0±0.1, and in some embodiments, 1:1.0±0.05. The niobium oxide may be $NbO_{0.7}$, $NbO_{1.0}$, $NbO_{1.1}$, and $NbO_2$.

The powder may be formed using any of a variety of processes known in the art, such as electron beam melting, reduction, etc. A tantalum powder, for instance, may be formed by reducing a tantalum salt (e.g., potassium fluotantalate ($K_2TaF_7$), sodium fluotantalate ($Na_2TaF_7$), tantalum pentachloride ($TaCl_5$), etc.) with an alkali reducing agent (e.g., sodium).

In yet other embodiments, the powder may also be formed by reacting an oxide of a valve metal compound with a reducing agent that contains a metal having a relatively high oxidation state (e.g., magnesium). The valve metal oxide is typically a tantalum and/or niobium oxide capable of being reduced, such as $Ta_2O_x$ (x≤5) (e.g., $Ta_2O_5$) or $Nb_2O_x$ (x≤5) (e.g., $Nb_2O_5$). The reducing agent may be provided in a gaseous, liquid, or solid state, and may also be in the form of the metal, as well as alloys or salts thereof. In one embodiment, for instance, a halide salt (e.g., chloride, fluoride, etc.) may be employed. If desired, other components may also be added before, during, or after the reaction, such as dopants, alkali metals, etc. The reduction of the oxide is typically carried out at a temperature of from about 400° C. to about 1200° C., and in some embodiments, from about 600° C. to about 1000° C., for about 20 to about 300 minutes. Heating may be carried out in a reactor under an inert atmosphere (e.g., argon or nitrogen atmosphere) so that a molten bath is formed. Suitable reactors may include, for instance, vertical tube furnaces, rotary kilns, fluid bed furnaces, multiple hearth furnaces, self-propagation high-temperature synthesis reactors, etc. The reactor may be maintained under inert gas until that the mass in the reaction vessel is cooled to ambient temperature. Additional details of such a reduction reaction may be described in U.S. Patent Publication Nos. 2003/0110890 to He, et al. and 2004/0163491 to Shekhter, et al. After the reduction, the product may be cooled, crushed, and washed to remove excess impurities or reactants.

The resulting powder may be a free-flowing, finely divided powder that contains primary particles having any of a variety of shapes, such as a relatively flat shape (e.g., flakes) or three-dimensional shape (e.g., nodular or angular). When three-dimensional particles are employed, such particles typically have a relatively low "aspect ratio", which is the average diameter or width of the particles divided by the average thickness ("D/T"). For example, the aspect ratio of the particles may be about 4 or less, in some embodiments about 3 or less, and in some embodiments, from about 1 to about 2. The powder may also have a relatively high specific surface area, such as about 1 square meter per gram ("$m^2/g$") or more, in some embodiments about 2 $m^2/g$ or more, and in some embodiments, from about 4 to about 30 $m^2/g$. The term "specific surface area" generally refers to surface area as determined by the physical gas adsorption (B.E.T.) method of Bruanauer, Emmet, and Teller, Journal of American Chemical Society, Vol. 60, 1938, p. 309, with nitrogen as the adsorption gas. The test may be conducted with a MONOSORB® Specific Surface Area Analyzer available from QUANTACHROME Corporation, Syosset, N.Y., which measures the quantity of adsorbate nitrogen gas adsorbed on a solid surface by sensing the change in thermal conductivity of a flowing mixture of adsorbate and inert carrier gas (e.g., helium).

The primary particles of the powder may also have a median size (D50) of from about 5 to about 250 nanometers, and in some embodiments, from about 10 to about 100 nanometers, such as using a laser particle size distribution analyzer made by BECKMAN COULTER Corporation (e.g., LS-230), optionally after subjecting the particles to an ultrasonic wave vibration of 70 seconds. Due to its high surface area and low particle size, the powder may have a high specific charge, such as greater than about 5,000 microFarads*Volts per gram ("µF*V/g"), in some embodiments from about 10,000 to about 80,000 µF*V/g, and in some embodiments, from about 15,000 to about 45,000 µF*V/g. As is known in the art, the specific charge may be determined by multiplying capacitance by the anodizing voltage employed, and then dividing this product by the weight of the anodized electrode body.

The powder (as well as the anode) may also have a relatively low alkali metal, carbon, and oxygen content. For example, the powder may have no more than about 50 ppm carbon or alkali metals, and in some embodiments, no more than about 10 ppm carbon or alkali metals. Likewise, the powder may have no more than about 0.15 ppm/µC/g oxygen, and in some embodiments, no more than about 0.10 ppm/µC/g oxygen. Oxygen content may be measured by LECO Oxygen Analyzer and includes oxygen in natural oxide on the tantalum surface and bulk oxygen in the tantalum particles. Bulk oxygen content is controlled by period of crystalline lattice of tantalum, which is increasing linearly with increasing oxygen content in tantalum until the solubility limit is achieved. This method was described in "Critical Oxygen Content In Porous Anodes Of Solid Tantalum Capacitors", Pozdeev-Freeman et al., Journal of Materials Science: Materials In Electronics 9, (1998) 309-311 wherein X-ray diffraction analysis (XRDA) was employed to measure period of crystalline lattice of tantalum. Oxygen in sintered tantalum anodes may be limited to thin natural surface oxide, while the bulk of tantalum is practically free of oxygen.

To facilitate the construction of the anode, certain additional components may also be included in the powder. For example, the powder may be optionally mixed with a binder and/or lubricant to ensure that the particles adequately adhere to each other when compacted or pressed to form the pellet. Suitable binders may include, for instance, poly(vinyl butyral); poly(vinyl acetate); poly(vinyl alcohol); poly(vinyl pyrollidone); cellulosic polymers, such as carboxymethylcellulose, methyl cellulose, ethyl cellulose, hydroxyethyl cellulose, and methylhydroxyethyl cellulose; atactic polypropylene, polyethylene; polyethylene glycol (e.g., Carbowax from Dow Chemical Co.); polystyrene, poly(butadiene/styrene); polyamides, polyimides, and polyacrylamides, high molecular weight polyethers; copolymers of ethylene oxide and propylene oxide; fluoropolymers, such as polytetrafluoroethylene, polyvinylidene fluoride, and fluoroolefin copolymers; acrylic polymers, such as sodium polyacrylate, poly(lower alkyl acrylates), poly(lower alkyl methacrylates) and copolymers of lower alkyl acrylates and methacrylates; and fatty acids and waxes, such as stearic and other soapy fatty acids, vegetable wax, microwaxes (purified paraffins), etc. The binder may be dissolved and dispersed in a solvent. Exemplary solvents may include water, alcohols, and so forth. When utilized, the percentage of binders and/or lubricants may vary from about 0.1% to about 8% by weight of the total mass. It should be understood, however, that binders and/or lubricants are not necessarily required in the present invention.

The resulting powder may be compacted to form a pellet using any conventional powder press device. For example, a press mold may be employed that is a single station compaction press containing a die and one or multiple punches. Alternatively, anvil-type compaction press molds may be used that use only a die and single lower punch. Single station compaction press molds are available in several basic types, such as cam, toggle/knuckle and eccentric/crank presses with varying capabilities, such as single action, double action, floating die, movable platen, opposed ram, screw, impact, hot pressing, coining or sizing. The powder may be compacted around an anode lead wire. The wire may be formed from any electrically conductive material, such as tantalum, niobium, aluminum, hafnium, titanium, etc., as well as electrically conductive oxides and/or nitrides of thereof.

Any binder/lubricant may be removed after pressing by heating the pellet under vacuum at a certain temperature (e.g., from about 150° C. to about 500° C.) for several minutes. Alternatively, the binder/lubricant may also be removed by contacting the pellet with an aqueous solution, such as described in U.S. Pat. No. 6,197,252 to Bishop, et al. Thereafter, the pellet is sintered to form a porous, integral mass. The pellet is typically sintered at a temperature of from about 800° C. to about 2000° C., in some embodiments from about 1200° C. to about 1800° C., and in some embodiments, from about 1500° C. to about 1700° C., for a time of from about 5 minutes to about 100 minutes, and in some embodiments, from about 8 minutes to about 15 minutes. This may occur in one or more steps. If desired, sintering may occur in an atmosphere that limits the transfer of oxygen atoms to the anode. For example, sintering may occur in a reducing atmosphere, such as in a vacuum, inert gas, hydrogen, etc. The reducing atmosphere may be at a pressure of from about 10 Torr to about 2000 Torr, in some embodiments from about 100 Torr to about 1000 Torr, and in some embodiments, from about 100 Torr to about 930 Torr. Mixtures of hydrogen and other gases (e.g., argon or nitrogen) may also be employed.

Upon sintering, the pellet shrinks due to the growth of metallurgical bonds between the particles. Because shrinkage generally increases the density of the pellet, lower press densities ("green") may be employed to still achieve the desired target density. For example, the target density of the pellet after sintering is typically from about 5 to about 8 grams per cubic centimeter. As a result of the shrinking phenomenon, however, the pellet need not be pressed to such high densities, but may instead be pressed to densities of less than about 6.0 grams per cubic centimeter, and in some embodiments, from about 4.5 to about 5.5 grams per cubic centimeter. Among other things, the ability to employ lower green densities may provide significant cost savings and increase processing efficiency.

The shape and size of the anode may vary as desired. For example, the anode may be shaped in the form of a D, square, rectangle, circle, oval, triangle, etc. Polygonal shapes having more than four (4) edges (e.g., hexagon, octagon, heptagon, pentagon, etc.) are particularly desired due to their relatively high surface area. The length of the anode may likewise range from about 1 to about 80 millimeters, in some embodiments from about 10 to about 60 millimeters, and in some embodiments, from about 20 to about 50 millimeters. The width of the anode may be from about 0.05 to about 40 millimeters, in some embodiments, from about 0.5 to about 25 millimeters, and in some embodiments, from about 2 to about 10 millimeters. The thickness of the anode may also be generally small to improve the electrical performance and volumetric efficiency of the resulting capacitor. Typically, the anode is planar and thus has a thickness of about 5 millimeters or less, in some embodiments, from about 0.05 to about 4 millimeters, and in some embodiments, from about 0.1 to about 3.5 millimeters. The ratio of the length of the anode to the thickness of the anode may be from about 5 to about 50, in some embodiments from about 6 to about 30, and in some embodiments, from about 7 to about 20.

As indicated above, the anode also contains a dielectric layer formed by anodically oxidizing ("anodizing") the sintered anode pellet. For example, a tantalum (Ta) anode may be anodized to tantalum pentoxide ($Ta_2O_5$). Typically, anodization is performed by initially applying an electrolyte to the pellet, such as by dipping the pellet into the electrolyte. A current is thereafter passed through the electrolyte to form the dielectric layer in the manner described above. The temperature at which the anodic oxidation process is conducted may vary as desired, but is typically from about 10° C. to about 200° C., in some embodiments from about 20° C. to about 150° C., and in some embodiments, from about 25° C. to about 90° C. The target forming voltage may likewise range from about 100 to about 500 volts, in some embodiments from about 150 to about 400 volts, and in some embodiments, from about 180 to about 300 volts.

The electrolyte is generally in the form of a liquid, such as a solution (e.g., aqueous or non-aqueous), dispersion, melt, etc. A solvent is generally employed in the electrolyte, such as water (e.g., deionized water); ethers (e.g., diethyl ether and tetrahydrofuran); alcohols (e.g., methanol, ethanol, n-propanol, isopropanol, and butanol); triglycerides; ketones (e.g., acetone, methyl ethyl ketone, and methyl isobutyl ketone); esters (e.g., ethyl acetate, butyl acetate, diethylene glycol ether acetate, and methoxypropyl acetate); amides (e.g., dimethylformamide, dimethylacetamide, dimethylcaprylic/capric fatty acid amide and N-alkylpyrrolidones); nitriles (e.g., acetonitrile, propionitrile, butyronitrile and benzonitrile); sulfoxides or sulfones (e.g., dimethyl sulfoxide (DMSO) and sulfolane); and so forth. The solvent may constitute from about 50 wt. % to about 99.9 wt. %, in some embodiments from about 75 wt. % to about 99 wt. %, and in some embodiments, from about 80 wt. % to about 95 wt. % of the electrolyte. Although not necessarily required, the use of an aqueous solvent (e.g., water) is often desired to facilitate formation of an oxide. In fact, water may constitute about 1 wt. % or more, in some embodiments about 10 wt. % or more, in some embodiments about 50 wt. % or more, in some embodiments about 70 wt. % or more, and in some embodiments, about 90 wt. % to 100 wt. % of the solvent(s) used in the electrolyte.

The electrolyte is electrically conductive and may have an electrical conductivity of about 1 milliSiemens per centimeter ("mS/cm") or more, in some embodiments about 10 mS/cm or more, and in some embodiments, from about 20 mS/cm to about 100 mS/cm, determined at a temperature of 25° C. To enhance the electrical conductivity of the electrolyte, a compound may be employed that is capable of dissociating in the solvent to form ions. Suitable ionic compounds for this purpose may include, for instance, acids, such as hydrochloric acid, nitric acid, sulfuric acid, phosphoric acid, polyphosphoric acid, boric acid, boronic acid, etc.; organic acids, including carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid, citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; sulfonic acids, such as methanesulfonic acid, benzenesulfonic acid, toluenesulfonic acid, trifluoromethanesulfonic acid, styrenesulfonic acid, naphthalene disulfonic acid, hydroxybenzenesulfonic acid, dodecylsulfonic acid, dodecylbenzenesulfonic acid, etc.; polymeric acids, such as poly(acrylic) or poly(methacrylic) acid and copolymers thereof (e.g., maleic-acrylic, sulfonic-acrylic, and styrene-acrylic copolymers), carageenic acid, carboxymethyl cellulose, alginic acid, etc.; and so forth. The concentration of ionic compounds is selected to achieve the desired electrical conductivity. For example, an acid (e.g., phosphoric acid) may constitute from about 0.01 wt. % to about 5 wt. %, in some embodiments from about 0.05 wt. % to about 0.8 wt. %, and in some embodiments from about 0.1 wt. % to about 0.5 wt. % of the electrolyte. If desired, blends of ionic compounds may also be employed in the electrolyte.

C. Solid Electrolyte

As indicated above, a solid electrolyte overlies the dielectric that generally functions as the cathode for the capacitor element and is formed from one or more layers. As explained in more detail below, at least one of the layers contains conductive polymer particles. For example, in one embodiment, the conductive polymer particles may be provided in a layer so that they are in direct contact with the dielectric layer. Still further, in certain embodiments, the solid electrolyte may contain multiple layers, each of which includes such particles. Regardless, the conductive polymer(s) employed are typically π-conjugated and have electrical conductivity after oxidation or reduction, such as an electrical conductivity of at least about 1 μS cm$^{-1}$ after oxidation. Examples of such π-conjugated conductive polymers include, for instance, polyheterocycles (e.g., polypyrroles, polythiophenes, polyanilines, etc.), polyacetylenes, poly-p-phenylenes, polyphenolates, and so forth. In one embodiment, for example, the polymer is a substituted polythiophene, such as those having the following general structure:

wherein,

T is O or S;

D is an optionally substituted $C_1$ to $C_5$ alkylene radical (e.g., methylene, ethylene, n-propylene, n-butylene, n-pentylene, etc.);

$R_7$ is a linear or branched, optionally substituted $C_1$ to $C_{18}$ alkyl radical (e.g., methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl, n-octadecyl, etc.);

optionally substituted $C_5$ to $C_{12}$ cycloalkyl radical (e.g., cyclopentyl, cyclohexyl, cycloheptyl, cyclooctyl, cyclononyl cyclodecyl, etc.); optionally substituted $C_6$ to $C_{14}$ aryl radical (e.g., phenyl, naphthyl, etc.); optionally substituted $C_7$ to $C_{18}$ aralkyl radical (e.g., benzyl, o-, m-, p-tolyl, 2,3-, 2,4-, 2,5-, 2-6, 3-4-, 3,5-xylyl, mesityl, etc.); optionally substituted $C_1$ to $C_4$ hydroxyalkyl radical, or hydroxyl radical; and q is an integer from 0 to 8, in some embodiments, from 0 to 2, and in one embodiment, 0; and n is from 2 to 5,000, in some embodiments, from 4 to 2,000, and in some embodiments, from 5 to 1,000. Example of substituents for the radicals "D" or "$R_7$" include, for instance, alkyl, cycloalkyl, aryl, aralkyl, alkoxy, halogen, ether, thioether, disulphide, sulfoxide, sulfone, sulfonate, amino, aldehyde, keto, carboxylic acid ester, carboxylic acid, carbonate, carboxylate, cyano, alkylsilane and alkoxysilane groups, carboxyamide groups, and so forth.

Particularly suitable thiophene polymers are those in which "D" is an optionally substituted $C_2$ to $C_3$ alkylene radical. For instance, the polymer may be optionally substituted poly(3,4-ethylenedioxythiophene), which has the following general structure:

Methods for forming conductive polymers, such as described above, are well known in the art. For instance, U.S. Pat. No. 6,987,663 to Merker, et al., describes various techniques for forming substituted polythiophenes from a monomeric precursor. The monomeric precursor may, for instance, have the following structure:

wherein,

T, D, $R_7$, and q are defined above. Particularly suitable thiophene monomers are those in which "D" is an optionally substituted $C_2$ to $C_3$ alkylene radical. For instance, optionally substituted 3,4-alkylenedioxythiophenes may be employed that have the general structure:

wherein, $R_7$ and q are as defined above. In one particular embodiment, "q" is 0. One commercially suitable example of 3,4-ethylenedioxythiophene is available from Heraeus Clevios under the designation Clevios™ M. Other suitable monomers are also described in U.S. Pat. No. 5,111,327 to Blohm, et al. and U.S. Pat. No. 6,635,729 to Groenendaal, et al. Derivatives of these monomers may also be employed that are, for example, dimers or trimers of the above monomers. Higher molecular derivatives, i.e., tetramers, pentamers, etc. of the monomers are suitable for use in the present invention. The derivatives may be made up of identical or different monomer units and used in pure form and in a mixture with one another and/or with the monomers. Oxidized or reduced forms of these precursors may also be employed.

The thiophene monomers may be polymerized in the presence of an oxidative catalyst. The oxidative catalyst may be a transition metal salt, such as a salt of an inorganic or organic acid that contain ammonium, sodium, gold, iron (III), copper(II), chromium(VI), cerium(IV), manganese (IV), manganese(VII), or ruthenium(III) cations. Particularly suitable transition metal salts include halides (e.g., $FeCl_3$ or $HAuCl_4$); salts of other inorganic acids (e.g., $Fe(ClO_4)_3$, $Fe_2(SO_4)_3$, $(NH_4)_2S_2O_8$, or $Na_3Mo_{12}PO_{40}$); and salts of organic acids and inorganic acids comprising organic radicals. Examples of salts of inorganic acids with organic radicals include, for instance, iron(III) salts of sulfuric acid monoesters of $C_1$ to $C_{20}$ alkanols (e.g., iron(III) salt of lauryl sulfate). Likewise, examples of salts of organic acids include, for instance, iron(III) salts of $C_1$ to $C_{20}$ alkane sulfonic acids (e.g., methane, ethane, propane, butane, or dodecane sulfonic acid); iron (III) salts of aliphatic perfluorosulfonic acids (e.g., trifluoromethane sulfonic acid, perfluorobutane sulfonic acid, or perfluorooctane sulfonic acid); iron (III) salts of aliphatic $C_1$ to $C_{20}$ carboxylic acids (e.g., 2-ethylhexylcarboxylic acid); iron (III) salts of aliphatic perfluorocarboxylic acids (e.g., trifluoroacetic acid or perfluorooctane acid); iron (III) salts of aromatic sulfonic acids optionally substituted by $C_1$ to $C_{20}$ alkyl groups (e.g., benzene sulfonic acid, o-toluene sulfonic acid, p-toluene sulfonic acid, or dodecylbenzene sulfonic acid); iron (III) salts of cycloalkane sulfonic acids (e.g., camphor sulfonic acid); and so forth. Mixtures of these above-mentioned salts may also be used.

If desired, polymerization of the monomer may occur in a precursor solution. Solvents (e.g., polar protic or nonpolar) may be employed in the solution, such as water, glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); alcohols (e.g., methanol, ethanol, n-propanol, iso-propanol, and butanol); ketones (e.g., acetone, methyl ethyl ketone, and methyl isobutyl ketone); esters (e.g., ethyl acetate, butyl acetate, diethylene glycol ether acetate, methoxypropyl acetate, ethylene carbonate, propylene carbonate, etc.); amides (e.g., dimethylformamide, dimethylacetamide, dimethylcaprylic/capric fatty acid amide and N-alkylpyrrolidones); sulfoxides or sulfones (e.g., dimethyl sulfoxide (DMSO) and sulfolane); phenolic compounds (e.g., toluene, xylene, etc.), and so forth. Water is a particularly suitable solvent for the reaction. When employed, the total amount of solvents in the precursor solution may be from about 40 wt. % wt. % to about 90 wt. %, in some embodiments from about 50 wt. % to about 85 wt. %, and in some embodiments, from about 60 wt. % to about 80 wt. %.

Polymerization of the thiophene monomer generally occurs at a temperature of from about 10° C. to about 100° C., and in some embodiments, from about 15° C. to about 75° C. Upon completion of the reaction, known filtration techniques may be employed to remove any salt impurities. One or more washing steps may also be employed to purify the dispersion.

Upon polymerization, the resulting conductive polymer is generally in the form of particles having a small size, such as an average diameter of from about 1 to about 200 nanometers, in some embodiments from about 2 to about 100 nanometers, and in some embodiments, from about 4 to about 50 nanometers. The diameter of the particles may be determined using known techniques, such as by ultracentrifuge, laser diffraction, etc. The shape of the particles may likewise vary. In one particular embodiment, for instance, the particles are spherical in shape. However, it should be understood that other shapes are also contemplated by the present invention, such as plates, rods, discs, bars, tubes, irregular shapes, etc. The concentration of the particles in the dispersion may vary depending on the desired viscosity of the dispersion and the particular manner in which the dispersion is to be applied to the capacitor. Typically, however, the particles constitute from about 0.1 to about 10 wt. %, in some embodiments from about 0.4 to about 5 wt. %, and in some embodiments, from about 0.5 to about 4 wt. % of the dispersion.

If desired, the formation of the conductive polymer into a particulate form may be enhanced by using a separate counterion to counteract a charged conductive polymer (e.g., polythiophene). That is, the conductive polymer (e.g., polythiophene or derivative thereof) used in the solid electrolyte typically has a charge on the main polymer chain that is neutral or positive (cationic). Polythiophene derivatives, for instance, typically carry a positive charge in the main polymer chain. In some cases, the polymer may possess positive and negative charges in the structural unit, with the positive charge being located on the main chain and the negative charge optionally on the substituents of the radical "R", such as sulfonate or carboxylate groups. The positive charges of the main chain may be partially or wholly saturated with the optionally present anionic groups on the radicals "R." Viewed overall, the polythiophenes may, in these cases, be cationic, neutral or even anionic. Nevertheless, they are all regarded as cationic polythiophenes as the polythiophene main chain has a positive charge.

The counterion may be a monomeric or polymeric anion. Polymeric anions can, for example, be anions of polymeric carboxylic acids (e.g., polyacrylic acids, polymethacrylic acid, polymaleic acids, etc.); polymeric sulfonic acids (e.g., polystyrene sulfonic acids ("PSS"), polyvinyl sulfonic acids, etc.); and so forth. The acids may also be copolymers, such as copolymers of vinyl carboxylic and vinyl sulfonic acids with other polymerizable monomers, such as acrylic acid esters and styrene. Likewise, suitable monomeric anions include, for example, anions of $C_1$ to $C_{20}$ alkane sulfonic acids (e.g., dodecane sulfonic acid); aliphatic perfluorosulfonic acids (e.g., trifluoromethane sulfonic acid, perfluorobutane sulfonic acid or perfluorooctane sulfonic acid); aliphatic $C_1$ to $C_{20}$ carboxylic acids (e.g., 2-ethyl-hexylcarboxylic acid); aliphatic perfluorocarboxylic acids (e.g., trifluoroacetic acid or perfluorooctanoic acid); aromatic sulfonic acids optionally substituted by $C_1$ to $C_{20}$ alkyl groups (e.g., benzene sulfonic acid, o-toluene sulfonic acid, p-toluene sulfonic acid or dodecylbenzene sulfonic acid); cycloalkane sulfonic acids (e.g., camphor sulfonic acid or tetrafluoroborates, hexafluorophosphates, perchlorates, hexafluoroantimonates, hexafluoroarsenates or hexachloroantimonates); and so forth. Particularly suitable counteranions are polymeric anions, such as a polymeric carboxylic or sulfonic acid (e.g., polystyrene sulfonic acid ("PSS")). The molecular weight of such polymeric anions typically ranges from about 1,000 to about 2,000,000, and in some embodiments, from about 2,000 to about 500,000.

When employed, the weight ratio of such counterions to conductive polymers in a given layer of the solid electrolyte is typically from about 0.5:1 to about 50:1, in some embodiments from about 1:1 to about 30:1, and in some embodiments, from about 2:1 to about 20:1. The weight of the electrically conductive polymers corresponds referred to the above-referenced weight ratios refers to the weighed-in portion of the monomers used, assuming that a complete conversion occurs during polymerization.

In addition to conductive polymer(s) and optional counterion(s), the dispersion may also contain one or more binders to further enhance the adhesive nature of the polymeric layer and also increase the stability of the particles within the dispersion. The binders may be organic in nature, such as polyvinyl alcohols, polyvinyl pyrrolidones, polyvinyl chlorides, polyvinyl acetates, polyvinyl butyrates, polyacrylic acid esters, polyacrylic acid amides, polymethacrylic acid esters, polymethacrylic acid amides, polyacrylonitriles, styrene/acrylic acid ester, vinyl acetate/acrylic acid ester and ethylene/vinyl acetate copolymers, polybutadienes, polyisoprenes, polystyrenes, polyethers, polyesters, polycarbonates, polyurethanes, polyamides, polyimides, polysulfones, melamine formaldehyde resins, epoxide resins, silicone resins or celluloses. Crosslinking agents may also be employed to enhance the adhesion capacity of the binders. Such crosslinking agents may include, for instance, melamine compounds, masked isocyanates or functional silanes, such as 3-glycidoxypropyltrialkoxysilane, tetraethoxysilane and tetraethoxysilane hydrolysate or crosslinkable polymers, such as polyurethanes, polyacrylates or polyolefins, and subsequent crosslinking.

Dispersion agents may also be employed to facilitate the formation of the solid electrolyte and the ability to apply it to the anode. Suitable dispersion agents include solvents, such as aliphatic alcohols (e.g., methanol, ethanol, i-propanol and butanol), aliphatic ketones (e.g., acetone and methyl ethyl ketones), aliphatic carboxylic acid esters (e.g., ethyl acetate and butyl acetate), aromatic hydrocarbons (e.g., toluene and xylene), aliphatic hydrocarbons (e.g., hexane, heptane and cyclohexane), chlorinated hydrocarbons (e.g., dichloromethane and dichloroethane), aliphatic nitriles (e.g., acetonitrile), aliphatic sulfoxides and sulfones (e.g., dimethyl sulfoxide and sulfolane), aliphatic carboxylic acid amides (e.g., methylacetamide, dimethylacetamide and dimethylformamide), aliphatic and araliphatic ethers (e.g., diethylether and anisole), water, and mixtures of any of the foregoing solvents. A particularly suitable dispersion agent is water.

In addition to those mentioned above, still other ingredients may also be used in the dispersion. For example, conventional fillers may be used that have a size of from about 10 nanometers to about 100 micrometers, in some embodiments from about 50 nanometers to about 50 micrometers, and in some embodiments, from about 100 nanometers to about 30 micrometers. Examples of such fillers include calcium carbonate, silicates, silica, calcium or barium sulfate, aluminum hydroxide, glass fibers or bulbs, wood flour, cellulose powder carbon black, electrically conductive polymers, etc. The fillers may be introduced into the dispersion in powder form, but may also be present in another form, such as fibers.

Surface-active substances may also be employed in the dispersion, such as ionic or non-ionic surfactants. Furthermore, adhesives may be employed, such as organofunctional silanes or their hydrolysates, for example 3-glycidoxypropyltrialkoxysilane, 3-aminopropyl-triethoxysilane, 3-mercaptopropyl-trimethoxysilane, 3-metacryloxypropyltrimethoxysilane, vinyltrimethoxysilane or octyltriethoxysilane. The dispersion may also contain additives that increase conductivity, such as ether group-containing compounds (e.g., tetrahydrofuran), lactone group-containing compounds (e.g., γ-butyrolactone or γ-valerolactone), amide or lactam group-containing compounds (e.g., caprolactam, N-methylcaprolactam, N,N-dimethylacetamide, N-methylacetamide, N,N-dimethylformamide (DMF), N-methylformamide, N-methylformanilide, N-methylpyrrolidone (NMP), N-octylpyrrolidone, or pyrrolidone), sulfones and sulfoxides (e.g., sulfolane (tetramethylenesulfone) or dimethylsulfoxide (DMSO)), sugar or sugar derivatives (e.g., saccharose, glucose, fructose, or lactose), sugar alcohols (e.g., sorbitol or mannitol), furan derivatives (e.g., 2-furancarboxylic acid or 3-furancarboxylic acid), an alcohols (e.g., ethylene glycol, glycerol, di- or triethylene glycol).

The polymeric dispersion may be applied by to the part using a variety of known techniques, such as by spin coating, impregnation, pouring, dropwise application, injection, spraying, doctor blading, brushing, printing (e.g., ink-jet, screen, or pad printing), or dipping. Although it may vary depending on the application technique employed, the viscosity of the dispersion is typically from about 0.1 to about 100,000 mPa-s (measured at a shear rate of 100 $s^{-1}$), in some embodiments from about 1 to about 10,000 mPa-s, in some embodiments from about 10 to about 1,500 mPa-s, and in some embodiments, from about 100 to about 1000 mPa-s. Once applied, the layer may be dried and washed.

One benefit of employing such a dispersion is that it may be able to penetrate into the edge region of the capacitor body to increase the adhesion to the dielectric. This results in a more mechanically robust part, which may reduce equivalent series resistance and leakage current. Such dispersions may also minimize the presence of ionic species (e.g., $Fe^{2+}$ or $Fe^{3+}$) produced during in situ polymerization, which can cause dielectric breakdown under high electric field due to ionic migration. Thus, by applying the conductive polymer as a dispersion rather through in situ polymerization, the resulting capacitor may exhibit a relatively high "breakdown voltage" (voltage at which the capacitor fails), such as about 100 volts or more, in some embodiments about 150 volts or more, in some embodiments about 200 volts or more, and in some embodiments, from about 220 volts to about 350 volts, as determined by increasing the applied voltage in increments of 3 volts until the leakage current reaches 1 mA.

If desired, the solid electrolyte may be formed from one or multiple layers. When multiple layers are employed, it is possible that one or more of the layers includes a conductive polymer formed by in situ polymerization. However, when it is desired to achieve very high breakdown voltages (e.g., from about 120 to 300 volts), the present inventors have discovered that the solid electrolyte is formed primarily from the polymeric dispersions described above, and that it is generally free of conductive polymers formed via in situ polymerization. Regardless of the number of layers employed, the resulting solid electrolyte typically has a total a thickness of from about 1 micrometer (μm) to about 200 μm, in some embodiments from about 2 μm to about 50 μm, and in some embodiments, from about 5 μm to about 30 μm.

The solid electrolyte may optionally be healed upon application to the anode. Healing may occur after each application of a solid electrolyte layer or may occur after the application of the entire coating if multiple layers are employed. In some embodiments, for example, the solid electrolyte may be healed by dipping the pellet into an electrolyte solution, such as a solution of acid, and thereafter applying a constant voltage to the solution until the current is reduced to a preselected level. If desired, such healing may be accomplished in multiple steps. After application of some or all of the layers described above, the resulting part may then be washed if desired to remove various byproducts, excess oxidizing agents, and so forth. Further, in some instances, drying may be utilized after some or all of the dipping operations described above. For example, drying may be desired after applying the oxidizing agent and/or after washing the pellet in order to open the pores of the part so that it can receive a liquid during subsequent dipping steps.

If desired, a hydroxyl-functional nonionic polymer may also be included in one or more layers of the solid electrolyte. The term "hydroxy-functional" generally means that the compound contains at least one hydroxyl functional group or is capable of possessing such a functional group in the presence of a solvent. Without intending to be limited by theory, it is believed that hydroxy-functional nonionic polymers can improve the degree of contact between the conductive polymer and the surface of the internal dielectric, which is typically relatively smooth in nature as a result of higher forming voltages. This unexpectedly increases the breakdown voltage and wet-to-dry capacitance of the resulting capacitor. Furthermore, it is believed that the use of a hydroxy-functional polymer with a certain molecular weight can also minimize the likelihood of chemical decomposition at high voltages. For instance, the molecular weight of the hydroxy-functional polymer may be from about 100 to 10,000 grams per mole, in some embodiments from about 200 to 2,000, in some embodiments from about 300 to about 1,200, and in some embodiments, from about 400 to about 800.

Any of a variety of hydroxy-functional nonionic polymers may generally be employed for this purpose. In one embodiment, for example, the hydroxy-functional polymer is a polyalkylene ether. Polyalkylene ethers may include polyalkylene glycols (e.g., polyethylene glycols, polypropylene glycols polytetramethylene glycols, polyepichlorohydrins, etc.), polyoxetanes, polyphenylene ethers, polyether ketones, and so forth. Polyalkylene ethers are typically predominantly linear, nonionic polymers with terminal hydroxy groups. Particularly suitable are polyethylene glycols, polypropylene glycols and polytetramethylene glycols (polytetrahydrofurans), which are produced by polyaddition of ethylene oxide, propylene oxide or tetrahydrofuran onto water. The polyalkylene ethers may be prepared by polycondensation reactions from diols or polyols. The diol component may be selected, in particular, from saturated or unsaturated, branched or unbranched, aliphatic dihydroxy compounds containing 5 to 36 carbon atoms or aromatic dihydroxy compounds, such as, for example, pentane-1,5-diol, hexane-1,6-diol, neopentyl glycol, bis-(hydroxymethyl)-cyclohexanes, bisphenol A, dimer diols, hydrogenated dimer diols or even mixtures of the diols mentioned. In addition, polyhydric alcohols may also be used in the polymerization reaction, including for example glycerol, di- and polyglycerol, trimethylolpropane, pentaerythritol or sorbitol.

In addition to those noted above, other hydroxy-functional nonionic polymers may also be employed in the present invention. Some examples of such polymers include, for instance, ethoxylated alkylphenols; ethoxylated or propoxylated $C_6$-$C_{24}$ fatty alcohols; polyoxyethylene glycol alkyl ethers having the general formula: $CH_3$—$(CH_2)_{10\text{-}16}$—$(O$—$C_2H_4)_{1\text{-}25}$—OH (e.g., octaethylene glycol monododecyl ether and pentaethylene glycol monododecyl ether); polyoxypropylene glycol alkyl ethers having the general formula: $CH_3$—$(CH_2)_{10\text{-}16}$—$(O$—$C_3H_6)_{1\text{-}25}$—OH; polyoxyethylene glycol octylphenol ethers having the following general formula: $C_8H_{17}$—$(C_6H_4)$—$(O$—$C_2H_4)_{1\text{-}25}$—OH (e.g., Triton™ X-100); polyoxyethylene glycol alkylphenol ethers having the following general formula: $C_8H_{19}$—$(C_6H_4)$—$(O$—$C_2H_4)_{1\text{-}25}$—OH (e.g., nonoxynol-9); polyoxyethylene glycol esters of $C_8$-$C_{24}$ fatty acids, such as polyoxyethylene glycol sorbitan alkyl esters (e.g., polyoxyethylene (20) sorbitan monolaurate, polyoxyethylene (20) sorbitan monopalmitate, polyoxyethylene (20) sorbitan monostearate, polyoxyethylene (20) sorbitan monooleate, PEG-20 methyl glucose distearate, PEG-20 methyl glucose sesquistearate, PEG-80 castor oil, and PEG-20 castor oil, PEG-3 castor oil, PEG 600 dioleate, and PEG 400 dioleate) and polyoxyethylene glycerol alkyl esters (e.g., polyoxyethylene-23 glycerol laurate and polyoxyethylene-20 glycerol stearate); polyoxyethylene glycol ethers of $C_8$-$C_{24}$ fatty acids (e.g., polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, polyoxyethylene-20 isohexadecyl ether, polyoxyethylene-15 tridecyl ether, and polyoxyethylene-6 tridecyl ether); block copolymers of polyethylene glycol and polypropylene glycol (e.g., Poloxamers); and so forth, as well as mixtures thereof.

The hydroxy-functional nonionic polymer may be incorporated into the solid electrolyte in a variety of different ways. In certain embodiments, for instance, the nonionic polymer may simply be incorporated into any conductive polymer layer(s) formed by a method as described above (e.g., pre-polymerized particle dispersion). In other embodiments, however, the nonionic polymer may be applied after the initial polymer layer(s) are formed.

D. Cathode Coating

If desired, the capacitor element may also contain a cathode coating that overlies the solid electrolyte and includes at least one carbonaceous layer and/or at least one metal layer that overlies the carbonaceous layer. The metal layer may act as a solderable conductor, contact layer, and/or charge collector for the capacitor, and may be formed from a conductive metal, such as copper, nickel, silver, nickel, zinc, tin, palladium, lead, copper, aluminum, molybdenum, titanium, iron, zirconium, magnesium, and alloys thereof. Silver is a particularly suitable conductive metal for use in the layer. The carbonaceous layer may limit contact between the metal layer and the solid electrolyte, which would otherwise increase the resistance of the capacitor. The carbonaceous layer may be formed from a variety of known carbonaceous materials, such as graphite, activated carbon, carbon black, etc.

E. Other Layers

Although not required, an external polymer coating may be applied to the anode body and overlie the solid electrolyte, optionally between the solid electrolyte and a cathode coating. The external polymer coating generally contains one or more layers formed from a dispersion of pre-polymerized conductive particles, such as described in more detail above. The external coating may be able to further penetrate into the edge region of the capacitor element to increase the adhesion to the dielectric and result in a more mechanically robust part, which may reduce equivalent series resistance and leakage current. If desired, a crosslinking agent may also be employed in the external polymer coating to enhance the degree of adhesion to the solid electrolyte. Typically, the crosslinking agent is applied prior to application of the dispersion used in the external coating. Suitable crosslinking agents are described, for instance, in U.S. Patent Publication No. 2007/0064376 to Merker, et al. and include, for instance, amines (e.g., diamines, triamines, oligomer amines, polyamines, etc.); polyvalent metal cations, such as salts or compounds of Mg, Al, Ca, Fe, Cr, Mn, Ba, Ti, Co, Ni, Cu, Ru, Ce or Zn, phosphonium compounds, sulfonium compounds, etc.

The capacitor element may also contain other layers. For example, a protective coating may optionally be formed between the dielectric and solid electrolyte, such as one made of a relatively insulative resinous material (natural or synthetic), such as shellac resins. These and other protective coating materials are described in more detail U.S. Pat. No. 6,674,635 to Fife, et al.

II. Terminations

The capacitor may also be provided with terminations, which may be in the form of pins, sheet, plate, frame, plate, pad, etc. For example, the capacitor may contain an anode termination to which the anode of the capacitor element is electrically connected and a cathode termination to which the cathode of the capacitor element is electrically connected. Any conductive material may be employed to form the terminations, such as a conductive metal (e.g., copper, nickel, silver, nickel, zinc, tin, palladium, lead, copper, aluminum, molybdenum, titanium, iron, zirconium, magnesium, and alloys thereof). Particularly suitable conductive metals include, for instance, copper, copper alloys (e.g., copper-zirconium, copper-magnesium, copper-zinc, or copper-iron), nickel, and nickel alloys (e.g., nickel-iron). One exemplary conductive material is a copper-iron alloy metal available from Wieland (Germany). If desired, the surface of the terminations may be electroplated with nickel, silver, gold, tin, etc. as is known in the art.

Figure 4:
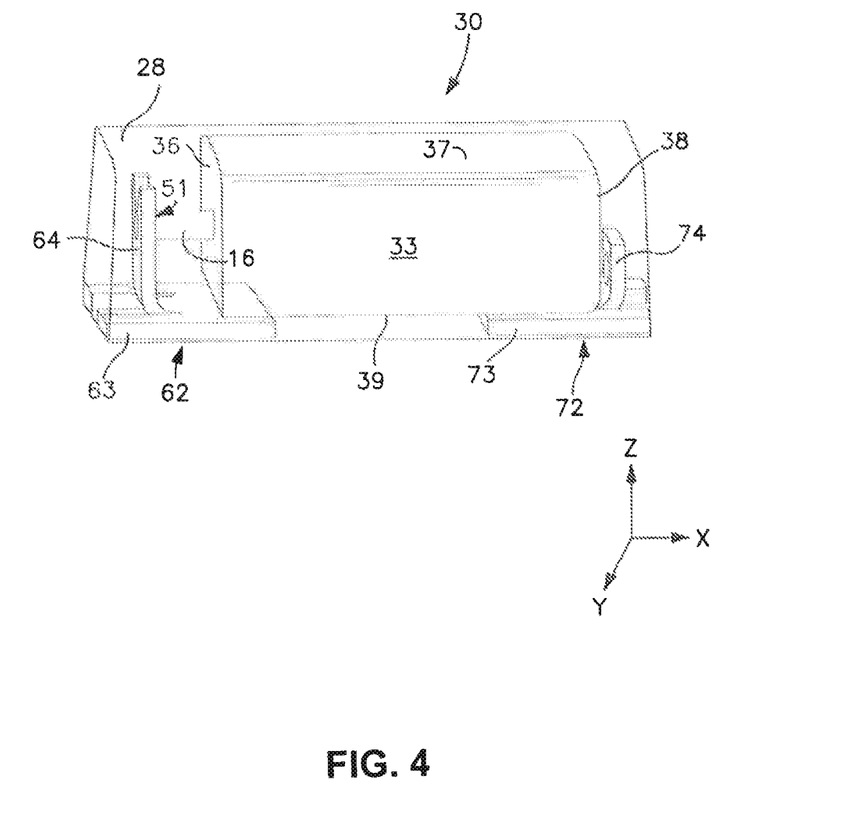
FIG. 4 is a schematic illustration of one embodiment of a capacitor that may be employed in the present invention.

Although by no means required, the capacitor may be surface mountable to the extent that the terminations are in relatively planar in nature, such as a frame or plate. Referring to FIG. 4, for example, one embodiment of a surface mountable electrolytic capacitor 30 is shown that includes an anode termination 62 and a cathode termination 72 in electrical connection with a capacitor element 33. The capacitor element 33 has an upper surface 37, lower surface 39, front surface 36, and rear surface 38. Although it may be in electrical contact with any of the surfaces of the capacitor element 33, the cathode termination 72 in the illustrated embodiment is in electrical contact with the lower surface 39 via a conductive adhesive (not shown). More specifically, the cathode termination 72 contains a first component 73 that is in electrical contact and generally parallel with the lower surface 39 of the capacitor element 33. The anode termination 62 likewise contains a first component 63 positioned substantially perpendicular to a second component 64. The first component 63 is in electrical contact and generally parallel with the lower surface 39 of the capacitor element 33. The second component 64 contains a region 51 that carries an anode lead 16. The region 51 may possess a "U-shape" to further enhance surface contact and mechanical stability of the lead 16.

The terminations may be connected to the capacitor element using any technique known in the art. In one embodiment, for example, a lead frame may be provided that defines the cathode termination 72 and anode termination 62. To attach the electrolytic capacitor element 33 to the lead frame, the conductive adhesive (not shown) may initially be applied to a surface of the cathode termination 72. The conductive adhesive may include, for instance, conductive metal particles contained with a resin composition. The metal particles may be silver, copper, gold, platinum, nickel, zinc, bismuth, etc. The resin composition may include a thermoset resin (e.g., epoxy resin), curing agent (e.g., acid anhydride), and coupling agent (e.g., silane coupling agents). Suitable conductive adhesives may be described in U.S. Patent Publication No. 2006/0038304 to Osako, et al. Any of a variety of techniques may be used to apply the conductive adhesive to the cathode termination 72. Printing techniques, for instance, may be employed due to their practical and cost-saving benefits.

A variety of methods may generally be employed to attach the terminations to the capacitor. In one embodiment, for example, the second component 64 of the anode termination 62 is initially bent upward to the position shown in FIG. 4. Thereafter, the capacitor element 33 is positioned on the cathode termination 72 so that its lower surface 39 contacts the adhesive 90 and the anode lead 16 is received by the region 51. If desired, an insulating material (not shown), such as a plastic pad or tape, may be positioned between the lower surface 39 of the capacitor element 33 and the first component 63 of the anode termination 62 to electrically isolate the anode and cathode terminations.

The anode lead 16 is then electrically connected to the region 51 using any technique known in the art, such as mechanical welding, laser welding, conductive adhesives, etc. For example, the anode lead 16 may be welded to the anode termination 62 using a laser. Lasers generally contain resonators that include a laser medium capable of releasing photons by stimulated emission and an energy source that excites the elements of the laser medium. One type of suitable laser is one in which the laser medium consist of an aluminum and yttrium garnet (YAG), doped with neodymium (Nd). The excited particles are neodymium ions $Nd^{3+}$. The energy source may provide continuous energy to the laser medium to emit a continuous laser beam or energy discharges to emit a pulsed laser beam. Upon electrically connecting the anode lead 16 to the anode termination 62, the conductive adhesive may then be cured. For example, a heat press may be used to apply heat and pressure to ensure that the electrolytic capacitor element 33 is adequately adhered to the cathode termination 72 by the adhesive.

III. Casing

Regardless of their particular nature (e.g., pins or surface mountable terminations), the capacitor element is generally encapsulated within a casing so that at least a portion of the anode and cathode terminations are exposed for electrical contact. As shown in FIG. 4, for instance, the capacitor element 33 is encapsulated within a casing 28 so that a portion of the anode termination 62 and a portion of the cathode termination 72 are exposed. The casing is typically formed from a resinous material, such as a thermoset resin. Examples of such resins include, for instance, epoxy resins, polyimide resins, melamine resins, urea-formaldehyde resins, polyurethane resins, phenolic resins, polyester resins, etc. Epoxy resins are also particularly suitable. Still other additives may also be employed, such as photoinitiators, viscosity modifiers, suspension aiding agents, pigments, stress reducing agents, non-conductive fillers, stabilizers, etc. For example, the non-conductive fillers may include inorganic oxide particles, such as silica, alumina, zirconia, magnesium oxide, iron oxide, copper oxide, zeolites, silicates, clays (e.g., smectite clay), etc., as well as composites (e.g., alumina-coated silica particles) and mixtures thereof.

As a result of the present invention, the capacitor(s) within the bank can exhibit excellent electrical properties for use in a medical device. For example, an individual capacitor within the bank may be also to withstand relatively high surge currents, which is commonly associated with high voltage medical devices. The peak surge current may be, for example, about 100 Amps or more, in some embodiments about 200 Amps or more, and in some embodiments, and in some embodiments, from about 300 Amps to about 800 Amps. In addition, the leakage current, which generally refers to the current flowing from one conductor to an adjacent conductor through an insulator, can be maintained at relatively low levels. For example, the numerical value of the normalized leakage current of a capacitor of the present invention may, in some embodiments, be less than about 1 $\mu A/\mu F^*V$, in some embodiments less than about 0.5 $\mu A/\mu F^*V$, and in some embodiments, less than about 0.1 $\mu A/\mu F^*V$, where $\mu A$ is microamps and $\mu F^*V$ is the product of the capacitance and the rated voltage.

The capacitor may also exhibit a high volumetric efficiency, such as from about 50,000 $\mu F^*V/cm^3$ to about 300,000 $\mu F^*V/cm^3$, in some embodiments from about 60,000 $\mu F^*V/cm^3$ to about 200,000 $\mu F^*V/cm^3$, and in some embodiments, from about 80,000 $\mu F^*V/cm^3$ to about 150,000 $\mu F^*V/cm^3$, determined at a frequency of 120 Hz and at room temperature (e.g., 25° C.). Volumetric efficiency is determined by multiplying the formation voltage of a part by its capacitance, and then dividing by the product by the volume of the part. For example, a formation voltage may be 175 volts for a part having a capacitance of 520 $\mu F$, which results in a product of 91,000 $\mu F^*V$. If the part occupies a volume of about 0.8 $cm^3$, this results in a volumetric efficiency of about 113,750 $\mu F^*V/cm^3$. Furthermore, the capacitor may exhibit a high energy density that enables it suitable for use in high pulse medical devices, such as defibrillators. Energy density is generally determined according to the equation $E=\frac{1}{2}*CV^2$, where C is the capacitance in farads (F) and V is the working voltage of capacitor in volts (V). The capacitance may, for instance, be measured using a capacitance meter (e.g., Keithley 3330 Precision LCZ meter with Kelvin Leads, 2 volts bias and 1 volt signal) at an operating frequency of 120 Hz and a temperature of 25° C. For example, the capacitor may exhibit an energy density of about 2.0 joules per cubic centimeter ($J/cm^3$) or more, in some embodiments about 3.0 $J/cm^3$, in some embodiments from about 4.0 $J/cm^3$ to about 10.0 $J/cm^3$, and in some embodiments, from about 4.5 to about 8.0 $J/cm^3$. The capacitance may likewise be about 1 milliFarad per square centimeter ("$mF/cm^2$") or more, in some embodiments about 2 $mF/cm^2$ or more, in some embodiments from about 5 to about 50 $mF/cm^2$, and in some embodiments, from about 8 to about 20 $mF/cm^2$.

Test Procedures

Capacitance:

The capacitance may be measured using a Keithley 3330 Precision LCZ meter with Kelvin Leads with 2.2 volt DC bias and a 0.5 volt peak to peak sinusoidal signal.

Equivalent Series Resistance (ESR):

Equivalence series resistance may be measured using a Keithley 3330 Precision LCZ meter with Kelvin Leads 2.2 volt DC bias and a 0.5 volt peak to peak sinusoidal signal. The operating frequency may be 100 kHz and the temperature may be room temperature.

Leakage Current:

Leakage current ("DCL") may be measured using a leakage test set that measures leakage current at room temperature and at the rated voltage after a minimum of 60 seconds.

Surge Current:

Surge current testing may be conducted at room temperature according to an article entitled "Surge in Solid Tantalum Capacitors", by John Gill. More particularly, surge testing may be performed using the circuit of FIG. 5.

Figure 5:
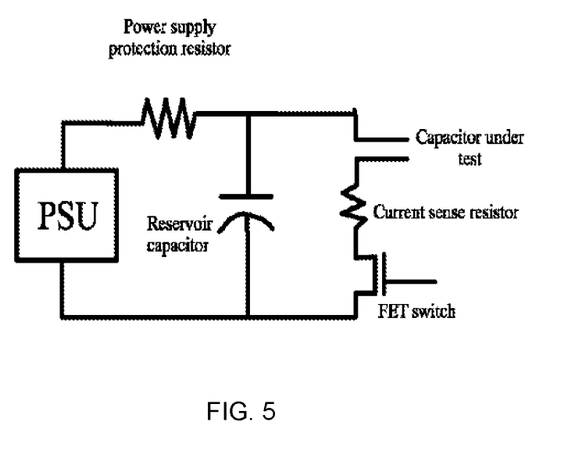
FIG. 5 illustrates a circuit for surge current testing.

The test sequence is generally as follows:
(a) An individual capacitor is charged up to the voltage when the capacitor is shorted (started from rated voltage);
(b) The probes are brought down on the capacitor. The switching FET is off at this stage so that no current will flow;
(c) The FET is turned on, thus allowing a fast instantaneous peak surge current to flow and charge the capacitor. The peak surge current is equivalent to ~2× the rated voltage of the part. For example, a capacitor with a rated voltage of 50 volts will have a peak surge current of about 100 Amps;
(d) The current is monitored by a resistor (e.g., 0.18 ohm resistor) in the source log of the transistor, and the part is dynamically rejected if its current is still not falling after a predetermined time based on the capacitance;
(e) The FET is turned off to stop the charging process; and
(f) Previous voltage and current before the capacitor shorted is recorded.

Breakdown Voltage:

Breakdown voltage testing may be conducted at room temperature. The test may be performed by charging an individual capacitor through the 10 kOhm resistor with 0.01 mAmps (charging slope dU/dt=1). When the applied voltage decreased more than 10%, the value of the breakdown voltage is recorded.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A capacitor bank for a medical device, the bank comprising two or more individual capacitors that are connected in series, wherein at least one of the capacitors in the bank comprises:

a capacitor element having a front surface and a lower surface, that contains an anode and a solid electrolyte, wherein the anode contains a sintered porous pellet and a dielectric layer formed thereon, and further wherein the solid electrolyte overlies the dielectric layer and contains a plurality of pre-polymerized conductive polymer particles;

an anode lead, wherein the anode lead extends from the front surface of the capacitor element;

an anode termination that is in electrical connection with the anode;

a cathode termination that is in electrical connection with the solid electrolyte; and a casing that encapsulates the capacitor element and leaves exposed at least a portion of the anode termination and the cathode termination;

wherein the capacitor bank exhibits an equivalent series resistance (ESR) of about 3 ohms or less measured at an operating frequency of 100 Hz; and wherein the capacitor bank provides a therapeutic high voltage of between about 500 volts to about 950 volts.

2. The capacitor bank of claim 1, wherein the dielectric layer includes tantalum pentoxide and the pellet includes tantalum.

3. The capacitor bank of claim 1, wherein the anode has a D-shape.

4. The capacitor bank of claim 1, wherein the pre-polymerized conductive polymer particles include a substituted polythiophene having the following general structure:

wherein, $R_7$ is a linear or branched, optionally substituted $C_1$ to $C_{18}$ alkyl radical; optionally substituted $C_6$ to $C_{14}$ aryl radical; optionally substituted $C_1$ to $C_4$ hydroxyalkyl radical, or hydroxyl radical;

q is an integer from 0 to 8; and n is from 2 to 5,000.

5. The capacitor bank of claim 1, wherein the pre-polymerized conductive polymer particles include poly(3,4-ethylenedioxythiophene) or a derivative thereof.

6. The capacitor bank of claim 1, wherein the pre-polymerized conductive polymer particles have an average diameter of from about 1 to about 200 nanometers.

7. The capacitor bank of claim 1, wherein the solid electrolyte also includes a hydroxyl-functional nonionic polymer.

8. The capacitor bank of claim 1, wherein the solid electrolyte is generally free of conductive polymers formed by in situ polymerization.

9. The capacitor bank of claim 1, wherein the solid electrolyte includes one or more layers, wherein the pre-polymerized conductive polymer particles are in a layer in direct contact with the dielectric layer.

10. The capacitor bank of claim 1, wherein the casing includes a resinous material.

11. The capacitor bank of claim 1, wherein the bank contains at least three capacitors.

12. The capacitor bank of claim 1, wherein multiple capacitors in the bank comprise:

a capacitor element having a front surface and a lower surface, that contains an anode and a solid electrolyte, wherein the anode contains a sintered porous pellet and a dielectric layer formed thereon, and further wherein the solid electrolyte overlies the dielectric layer and contains a plurality of pre-polymerized conductive polymer particles;

an anode lead, wherein the anode lead extends from the front surface of the capacitor element;

an anode termination that is in electrical connection with the anode;

a cathode termination that is in electrical connection with the solid electrolyte; and a casing that encapsulates the capacitor element and leaves exposed at least a portion of the anode termination and the cathode termination.

13. A medical device that comprises a capacitor bank provided within a housing, wherein the bank comprises two or more individual capacitors that are connected in series, wherein at least one of the capacitors in the bank comprises:

a capacitor element having a front surface and a lower surface, that contains an anode and a solid electrolyte, wherein the anode contains a sintered porous pellet and a dielectric layer formed thereon, and further wherein the solid electrolyte overlies the dielectric layer and contains a plurality of pre-polymerized conductive polymer particles;

an anode lead, wherein the anode lead extends from the front surface of the capacitor element;

an anode termination that is in electrical connection with the anode;

a cathode termination that is in electrical connection with the solid electrolyte; and a casing that encapsulates the capacitor element and leaves exposed at least a portion of the anode termination and the cathode termination;

wherein the capacitor bank exhibits an equivalent series resistance (ESR) of about 3 ohms or less measured at an operating frequency of 100 Hz; and wherein the capacitor bank provides a therapeutic high voltage of between about 500 volts to about 950 volts.

14. The medical device of claim 13, wherein the device is an implantable defibrillator.

15. The medical device of claim 14, further comprising one or more leads that are capable of being electrically coupled between the device and a patient's heart.

16. The medical device of claim 13, wherein the capacitor bank is coupled to a battery.

* * * * *